US007923459B2

(12) United States Patent
Gauthier et al.

(10) Patent No.: US 7,923,459 B2
(45) Date of Patent: Apr. 12, 2011

(54) PROCESS FOR THE SYNTHESIS OF 4-(3-METHANESULFONYLPHENYL)-1-N-PROPYL-PIPERIDINE

(75) Inventors: Donald R. Gauthier, Westfield, NJ (US); Richard Desmond, Lebanon, NJ (US); Paul N. Devine, Tinton Falls, NJ (US)

(73) Assignee: NSAB, Filial AF Neurosearch Sweden AB, Sverige, Ballerup (DK)

( * ) Notice: Subject to any disclaimer, the term of this patent is extended or adjusted under 35 U.S.C. 154(b) by 170 days.

(21) Appl. No.: 11/733,512

(22) Filed: Apr. 10, 2007

(65) Prior Publication Data

US 2007/0238879 A1    Oct. 11, 2007

Related U.S. Application Data

(63) Continuation of application No. PCT/EP2005/011020, filed on Oct. 13, 2005, now abandoned.

(60) Provisional application No. 60/618,196, filed on Oct. 13, 2004.

(51) Int. Cl.
*A61K 31/445* (2006.01)
(52) U.S. Cl. ...................................................... 514/317
(58) Field of Classification Search .................. 546/236; 514/317
See application file for complete search history.

(56) References Cited

U.S. PATENT DOCUMENTS

| 3,326,916 | A | 6/1967 | Creighton et al. |
| 3,539,573 | A | 11/1970 | Schmutz et al. |
| 4,048,314 | A | 9/1977 | Kubela et al. |
| 4,202,898 | A | 5/1980 | Depoortere |
| 4,333,942 | A | 6/1982 | Eistetter et al. |
| 4,415,736 | A | 11/1983 | Ciganek et al. |
| 4,485,109 | A | 11/1984 | Ciganek |
| 4,504,660 | A | 3/1985 | Klaubert et al. |
| 5,462,947 | A | 10/1995 | Svensson et al. |
| 5,502,050 | A | 3/1996 | Gross |
| 6,175,015 | B1 | 1/2001 | Yuan et al. |
| 2003/0109532 | A1 | 6/2003 | Sonesson et al. |

FOREIGN PATENT DOCUMENTS

| EP | 0060179 | 2/1982 |
| EP | 0369887 | 11/1989 |
| EP | 0094159 | 3/1990 |
| EP | 0533266 | 9/1992 |
| EP | 0533267 | 9/1992 |
| EP | 0533268 | 3/1993 |
| EP | 675118 | 4/1995 |
| EP | 0867183 | 9/1998 |
| EP | 0867183 | 10/2004 |
| FR | 1459013 | 5/1965 |
| GB | 850662 | 10/1957 |
| GB | 1060160 | 7/1965 |
| GB | 1060160 | 3/1967 |
| GB | 1560271 | 1/1977 |
| GB | 2078746 | 6/1981 |
| GB | 2083476 | 9/1981 |
| GB | 2027703 | 12/2006 |
| NL | 6510107 | 2/1966 |
| WO | 8905799 | 6/1989 |
| WO | 9109594 | 7/1991 |
| WO | 9218475 | 10/1992 |
| WO | 9300313 | 1/1993 |
| WO | 9304684 | 3/1993 |
| WO | 9811068 | 3/1998 |
| WO | 0003713 | 1/2000 |
| WO | 0078728 | 12/2000 |
| WO | 01/46144 | 6/2001 |
| WO | 01/46145 | 6/2001 |
| WO | 0146144 | 6/2001 |
| WO | 0146145 | 6/2001 |
| WO | 0146146 | 6/2001 |
| WO | 0205819 | 1/2002 |
| WO | 02059108 | 8/2002 |
| WO | 2004099150 | 11/2004 |
| WO | 2005019215 | 3/2005 |
| WO | 2005121087 | 12/2005 |
| WO | 2005121088 | 12/2005 |
| WO | 2005121092 | 12/2005 |
| WO | 2006039325 | 4/2006 |
| WO | 2006040155 | 4/2006 |
| WO | 2006040156 | 4/2006 |
| WO | 2007042295 | 4/2007 |
| WO | 2007065655 | 6/2007 |

OTHER PUBLICATIONS

Sato et al., "Oxidation of sulfides to sulfoxides and sulfones with 30% hydrogen peroxide under organic solvent- and halogen-free conditions" Tetrahedron 57 (2001) pp. 2469-2476.
Radl et al., "Synthesis of piperidine analogs of 1-(3-chlorophenyl) piperazine, a well known serotonin ligand" STN Accession No. 1996:661865, Abstract of Journal of Heterocyclic Chemistry (1999), 36(4).
Rosenfeld et al., "Gas chromatographic method for analysis of butyrophenones based on the Hofmann degradation reaction" STN Accession No. 1977:60610, Abstract of Journal of Chromatography (1976), 129.
Morita et al., "Practical Application of the Palladium-catalyzed Animation in Phenylpiperazine Synthesis: An Efficient Synthesis of a Metabolite of the Antipsychotic Agent Aripiprazole"; 1998 Elsevier Science Ltd., pp. 4811-4818.
Smaill et al., "Mono-and difuntional nitrogen mustard analogues of the DNA minor groove binder pibenzimol synthesis, cytotoxity and interaction with DNA", Anti-Cancer Drug Design (1998), vol. 13, Oxford University Press; pp. 221-242.

(Continued)

*Primary Examiner* — Rita J Desai
*Assistant Examiner* — John Mabry
(74) *Attorney, Agent, or Firm* — Birch, Stewart, Kolasch & Birch, LLP

(57) ABSTRACT

The present invention is directed to processes for the preparation of 4-(3-methanesulfonyl-phenyl)-1-N-propylpiperidine (I) or a pharmaceutically acceptable salt thereof, which comprises: oxidizing a sulfide of the formula (II): with a catalytic oxidizing agent and an oxidant; to give a compound of the formula (III): followed by catalytic reduction of the compound of formula (III).

15 Claims, No Drawings

OTHER PUBLICATIONS

Beugelmans et al., "Synthese d'heterocycles a 5 et 6 chainons par une strategie combinant des reactions SNAr et SRN1"; Institut de Chimie des Substances Naturelles, 1995 vol. 132; pp. 306-313.

Egawa et al., A New Synthesis of 7H-Pyrido[1,2,3-de][1,4]benzoxazine Derivatives Including an Antibacterial Agent, Ofloxacin:; Research Labortories, Osaka, Japan; 1986 vol. 34, pp. 4098-4102.

Takai et al., "Reaction of Spiro[4H-3, 1-benzoxaxine-44'-piperidin]-2(1H)-one Derivatives and Related Compounds with Phosphorus Oxychloride"; Tokyo Research Laboratory, Tokyo, Japan; pp. 1901-1906.

Zhang et al., "Acta Pharmaceutica Sinica"; 1981; vol. 16, No. 6; pp. 414-424; Shanghai Institut of Pharmaceutical Industrial Research; Shanghai.

Klaubert et al., "N-(Aminohenyl)oxamic Acids and Esters as Potent, Orally Active Antiallergy Agents"; 1989 American Chemical Society; Research Division, Wyeth Laboratories Inc., Radnor, Pennsylvania; Journal of Medicinal Chemistry, vol. 24; pp. 742-748.

Self et al., "Cine and tele Substitutions in the Reaction of 2,3-Dinitroaniline with Secondary Amines"; J.C.S. Chem. Comm., 1980; pp. 281-282.

Elslager et al., "Folate Antagonists. 3. 2,4-Diamino-6-(heterocyclic)quinazolines, a Novel Class of Antimetabolits with Potent Antimalarial and Antibacterial Activity"; Journal of Medicinal Chemistry; 1972 vol. 15, No. 87; pp. 826-836; Department of Chemistry, Research and Development Division, Ann Arbor, Michigan.

Berberian et al., "Comparison of Schistosomicidal Activity of Xanthenones and 4-Methyl-3-chloroanilines and Their Hydroxymethyl Analogs in Swiss Mice and Syrian Hamsters Infected with *Schistosoma mansoni*"; Sterlin-Winthrop Research Institute, Rensselaer, New York, pp. 607-610, 1969.

David W. Henry, A Facile Synthesis of Piperazines from Primary Amines (1); Department of Pharmaceutical Chemistry, Stanford Research Institute; Dec. 1966; pp. 503-511.

Bergel et al., Synthetic Analgesics, Part 1. Synthesis of Basic Benzofuran Derivatives and Certain 4-Phenylpiperidine Compounds; 1944; pp. 261-265.

Nacci et al., "Antiblastic substances L11. Tylophorien analogs. 1. Synthesis and cytostotic and cytotoxic activity of 4-(3,4-dimethoxphenyl)piperidine"; Farmaco E. Scintifica 1972, 328, (5) pp. 399-410.

Sonesson et al., "Substituted (S)-Phenylpiperidines and Rigid Congeners as Preferential Dopamine Autoreceptor Antagonists: Synthesis and Structure-Activity Relationships"; Journal of Medicinal Chemistry, 1994 American Chemical Society; pp. 2735-2752.

Radl et al., "Synthesis of Piperidine Analogs of 1-(3-Chlorophenyl)piperazine, a Well Known Serotonin Ligand"; Research Institute for Pharmacy and Biochemistry, Prague, Czech Republic; pp. 1017-1022, 1999.

Altomare et al., Quantitative Structure-Metabolim Relationship Analyses of MAO-Medicated Toxication of 1-Methyl-4-phenyl-1,2,3,6-tetrahydropyridine and Alalogues; Chem. Res. Toxicol, 1992, vol. 5, pp. 366-375.

Carlsson et al., Interactions between glutamatergic and monoaminergic systems within the basal nanglia—implications for schizophrenia and Parkinson's disease; Department of Pharmacology, University of Goteborg, Goteborg, Sweden; 1990 Elsevier Science Publishers; vol. 13, No. 7, 1990; pp. 272-276.

Coyle et al., "Alzheimer's Disease: A Disorder of Cortical Cholinergic Innervation"; Science, vol. 219, Johns Hopkins School of Medicine, Baltimore, Maryland; pp. 1184-1190, 1983.

Feldman et al., 1993; "Mind-Altering Drugs"; Chapter 17; pp. 731, 762 and 763.

Grunblatt et al., "Potent neuroprotective and antioxidant activity of apomorhine in PMTP and 6-hydroxydopamine induced neurotoxicity"; Journal Neural transm. (1999) [Suppl]I pp. 57-70.

Grunblatt et al., "Neuroprotective Strategies in Parkinson's Disease Using Models of 6-Hydroxydopamine and MPTP"; Bruce Rappaport Family Research Institute and Department of Pharmacology, Haifa, Israel; pp. 262-273, 2000.

Philip G. Strange; "Antipsychotic Drugs: Importance of Dopamine Receptors for Mechanisms of Therapeutic Actions and Side Effects"; School of Animal and Microbial Sciences, University of Reading, Whiteknights, Reading, United Kingdom, vol. 53, No. 1; pp. 119-133, 2001.

Manfred E. Wolff; "Antipsychotic Agents, 4.1 Biologic Test Methods"; Burger's Medicinal Chemistry; 4th Edition, Part III; John Wiley & Sons; 1979, pp. 872-873.

Roth et al., "Biochemical Pharmacology of Midbrain Dopamine Neurons"; Chapter 21; Yale University of Medicine; New Haven, CT; pp. 227 and 237, 1995.

Moore et al., "Dopaminergic Neuronal Systems in the Hypothalamus"; Department of Pharmacology and Toxicology, Michigan State University, East Lansing,Michigan; Chapter 22; pp. 245 and 254, 1995.

Michel Le Moal., "Mesocorticolimbic Dopaminergic Neurons Functional and Regulatory Roles"; Universite de Bordeaux, Bordeaux, France; Chapter 25, pp. 283 and 292, 1995.

Philip Seeman., "Dopamine Receptors Clinical Correlates"; Departmants of Pharmacology and Psychiatry, University of Toronto, Toronto, Ontario, Canada; Chapter 26, pp. 295-301, 1995.

George F. Koon; "Animal Models of Drug Addiction"; Department of Neuropharmacology, The Scripps Research Institute, Lo Jolla, California; Chapter 66, pp. 759, 745-746, 760, 744 and 1725, 1995.

Geyer et al., "Animal Models of Psychiatric Disorders"; Department of Neuropharmacology, The Scripps Research Institute, La Jolla, California; Chapter 68, pp. 787 and 793-795, 1995.

Paul Willner; "Dopaminergic Mechanisms in Depression and Mania"; Department of Psychology, University College of Swansea, Wales, United Kingdom; Chapter 80; pp. 921-928, 1995.

Bunney et al., "Schizophrenia and Glutamate"; Department of Pharmacology, University of Goteborg, Goteborg, Sweden; Chapter 101; pp. 1205 and 1207-1209, 1995.

Price et al., "Pharmacological Challenges in Anxiety Disorders"; University of Florida College of Medicine, Gainesville, Florida; Chapter 111; pp. 1311, 1317-1318 and 1320, 1995.

Amos D. Korczyn: "Parkinson's Disease", Tel Aviv University, Rama Aviv, Israel; Chapter 126; pp. 1479-1482, 1995.

George A. Bray; "Obesity, Fat Intake, and Chronic Disease"; Pennington Biomedical Research Center, Louisiana State University, Baton Rouge, Louisiana; Chapter 137; pp. 1591 and 1600, 1995.

Katherine A. Halmi; "Basic Biological Overview of Eating Disorders"; Cornell Medical Center—Westchester Division, White Plains, New York; Chapter 138; pp. 1609-1610 and 1612, 1995.

Manoury et al., Synthesis and Analgesic Activities of Some (4-Substituted phenyl-1-1-piperazinyl)alkyl 2-Aminobenzoates and 2-Aminonicotinates; Journal of Medicinal Chemistry, 1979, vol. 22, No. 5; pp. 554-559.

Oshiro et al., "Novel Antipsychotic Agents with Dopamine Autoreceptor Agonist Properties; Synthesis and Pharmacology of 7-[4-(4-Phenyl-1-piperanyl)butoxyl-3,4-dihydro-2(1H)-quinolinone Derivatives"; J. Med. Chemistry, 1998, pp. 658-667.

Sato et al., Oxidation of sulfides to sulfoxides and sulfones with 30% hydrogen peroxide under organic solvent-and halogen-free conditions; Department of Chemistry and Research Center for Materials Science; Nagoya University, Nagoya, Japan; pp. 2469-2476, 2001.

PROCESS FOR THE SYNTHESIS OF 4-(3-METHANESULFONYLPHENYL)-1-N-PROPYL-PIPERIDINE

The present application is a continuation of PCT Application No. PCT/EP2005/011020, filed on Oct. 13, 2005, and claims priority to U.S. Provisional Application Ser. No. 60/618,196, filed on Oct. 13, 2004. Both of which are incorporated herein by reference in their entireties.

BACKGROUND OF THE INVENTION 4-(3-Methanesulfonylphenyl)-1-n-propylpiperidine is useful as a modulator of dopamine neurotransmission and has therapeutic application for example in the treatment of Alzheimer's disease, Parkinson's disease and schizophrenia. Synthetic methods to prepare 4-(3-methanesulfonylphenyl)-1-n-propylpiperidine have been described in PCT Patent Publication WO 01/46145.

In accordance with the present invention, processes are provided for the preparation of 4-(3-methanesulfonylphenyl)-1-n-propylpiperidine, and pharmaceutically acceptable salts thereof. The subject process provide 4-(3-methanesulfonylphenyl)-1-N-propylpiperidine in high yield and purity while minimizing the number of synthetic steps.

SUMMARY OF THE INVENTION

The present invention is directed to processes for the preparation of 4-(3-methane-sulfonylphenyl)-1-n-propylpiperidine of the formula I:

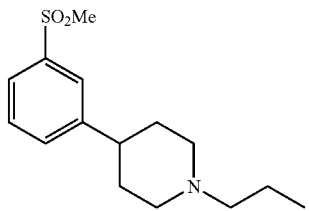

and pharmaceutically acceptable salts thereof.

DETAILED DESCRIPTION OF THE INVENTION

The present invention relates to processes for the preparation of 4-(3-methanesulfonyl-phenyl)-1-n-propylpiperidine which is useful as a pharmaceutical agent.

An embodiment of the present invention is directed to a process for the preparation of 4-(3-methanesulfonylphenyl)-1-n-propylpiperidine of the formula I:

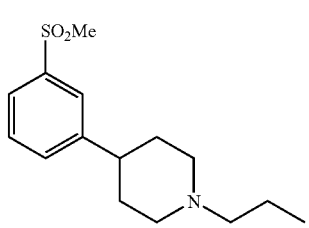

or a pharmaceutically acceptable salt thereof, which comprises:
oxidizing a sulfide of the formula II:

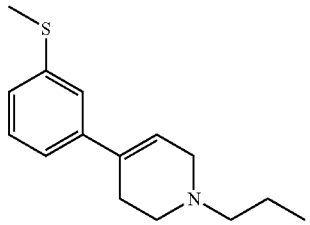

with a catalytic oxidizing agent and an oxidant;
to give a compound of the formula III:

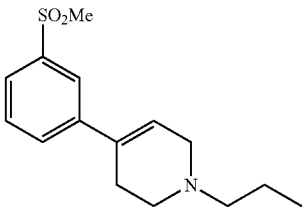

followed by catalytic reduction of the compound of the formula III;
to give the compound of the formula (I):

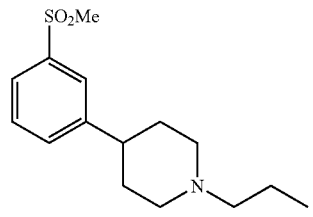

or a pharmaceutically acceptable salt thereof.

A further embodiment of the present invention is directed to a process for the preparation of 4-(3-methanesulfonylphenyl)-1-n-propylpiperidine of the formula (I):

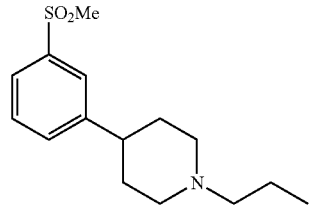

or a pharmaceutically acceptable salt thereof,
which further comprises:
dehydrating an alcohol of the formula Ia:

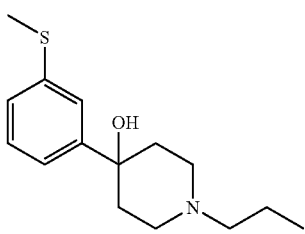

with a strong acid;

to give a sulfide of the formula II:

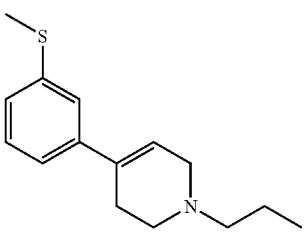

oxidizing the sulfide of the formula II with a catalytic oxidizing agent and an oxidant;
to give a compound of the formula III:

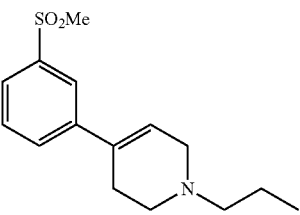

followed by catalytic reduction of the compound of the formula III;
to give the compound of the formula (I):

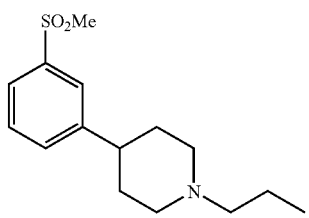

or a pharmaceutically acceptable salt thereof.

In an embodiment of the present invention the strong acid is a strong inorganic acid or a strong organic acid. In an embodiment of the present invention the strong acid is selected from sulfuric acid, hydrochloric acid, hydrofluoric acid, nitric acid and trifluoroacetic acid. Optionally, the dehydration of the alcohol of the formula Ia with a strong acid is conducted in a solvent. In an embodiment of the present invention the solvent is selected from toluene, xylene, hexanes and water.

In an embodiment of the present invention the catalytic oxidizing agent is a tungsten, ruthenium, molybdenum, osmium or chromium oxidizing agent.

In an embodiment of the present invention the catalytic oxidizing agent is a tungsten oxidizing agent. In an aspect of this embodiment, the tungsten oxidizing agent is sodium tungstate.

In an embodiment of the present invention the oxidant is a peroxide. In an aspect of this embodiment, the peroxide is sodium peroxide, hydrogen peroxide, sodium hypochlorite, sodium bromate, sodium periodate, peroxyacetic acid or peroxybenzoic acid. In a further aspect of this embodiment, the peroxide is sodium peroxide. Within this embodiment, the peroxide is an aqueous solution of sodium peroxide.

In an embodiment of the present invention the step of oxidizing the sulfide of the formula II is conducted at less than 3 pH. Within this embodiment, the step of oxidizing the sulfide of the formula II is conducted at less than 2 pH. Further within this embodiment, the step of oxidizing the sulfide of the formula II is conducted at less than 1 pH.

In an embodiment of the present invention the step of oxidizing the sulfide of the formula II is conducted at a temperature greater than 30° C. (inclusive). Within this embodiment, the step of oxidizing the sulfide of the formula II is conducted at a temperature greater than 40° C. (inclusive). Further within this embodiment, the step of oxidizing the sulfide of the formula II is conducted at a temperature between 40° C. and 60° C. (inclusive). Further within this embodiment, the step of oxidizing the sulfide of the formula II is conducted at a temperature between 50° C. and 55° C. (inclusive).

Preferred solvents for conducting the step of oxidizing the sulfide of the formula II comprise an aqueous solution with an organic solvent which is selected from toluene, tetrahydrofuran (THF), diethyl ether, diglyme and methyl t-butyl ether. The most preferred organic solvent is toluene.

In an embodiment of the present invention the step of catalytic reduction of the compound of the formula III comprises catalytic hydrogenation. Within this embodiment, the step of catalytic reduction of the compound of the formula III comprises catalytic hydrogenation with a palladium catalyst, a platinum catalyst or a ruthenium catalyst. Within this embodiment, the step of catalytic reduction of the compound of the formula III comprises catalytic hydrogenation with a palladium catalyst. Within this embodiment, the step of catalytic reduction of the compound of the formula III comprises catalytic hydrogenation with a palladium on carbon catalyst. Further within this embodiment, the step of catalytic reduction of the compound of the formula III comprises catalytic hydrogenation with a 10% palladium on carbon catalyst or a 5% palladium on carbon catalyst.

In an alternate embodiment of the present invention the step of catalytic reduction of the compound of the formula III comprises catalytic transfer hydrogenation. Within this embodiment, the step of catalytic reduction of the compound of the formula III comprises catalytic transfer hydrogenation with a rhodium catalyst or a ruthenium catalyst and a hydrogen transfer source. Within this embodiment, the rhodium catalyst may be selected from bis((pentamethylcyclopentadienyl)rhodium chloride) and bis((cyclopentadienyl)rhodium chloride), optionally in the presence of alternate ligands. Within this embodiment, the ruthenium catalyst may be selected from bis((4-isopropyl-toluenyl)ruthenium chloride) and bis((cyclopenta-dienyl)ruthenium chloride), optionally in the presence of alternate ligands. Within this embodiment, the hydrogen transfer source may be an acid or an alcohol, such as formic acid, methanol, ethanol, isopropanol, isobutanol or n-butanol. In this embodiment, a base is optionally present with the hydrogen transfer source. The base may be an inorganic base such as a base selected from potassium or sodium hydroxide, potassium or sodium carbonate, potassium or sodium bicarbonate potassium or sodium alkoxides, and the like. The alkoxides can be derived from lower ($C_1$-$C_5$) or higher (>$C_6$) primary, secondary or tertiary alcohols.

Solvents for conducting the step of catalytic reduction of the compound of the formula III include an aqueous solution with an alcohol, such as an alcohol selected from methanol, ethanol, isopropanol, isobutanol or n-butanol. Within this embodiment, the alcohol may be methanol.

The term "pharmaceutically acceptable salts" refers to salts prepared from pharmaceutically acceptable non-toxic bases or acids including inorganic or organic bases and inorganic or organic acids. Salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are benzenesulfonic, citric, hydrobromic, hydrochloric, maleic, famaric, succinic and tartaric acids. It will be understood that, as used herein, references to the compounds of the present invention are meant to also include the pharmaceutically acceptable salts.

The starting materials and reagents for the subject processes are either commercially available or are known in the literature or may be prepared following literature methods described for analogous compounds. The skills required in carrying out the reaction and purification of the resulting reaction products are known to those in the art. Purification procedures include crystallization, distillation, normal phase or reverse phase chromatography.

The following Examples are provided by way of illustration only, and in no way are meant to limit the scope of the invention.

EXAMPLE 1

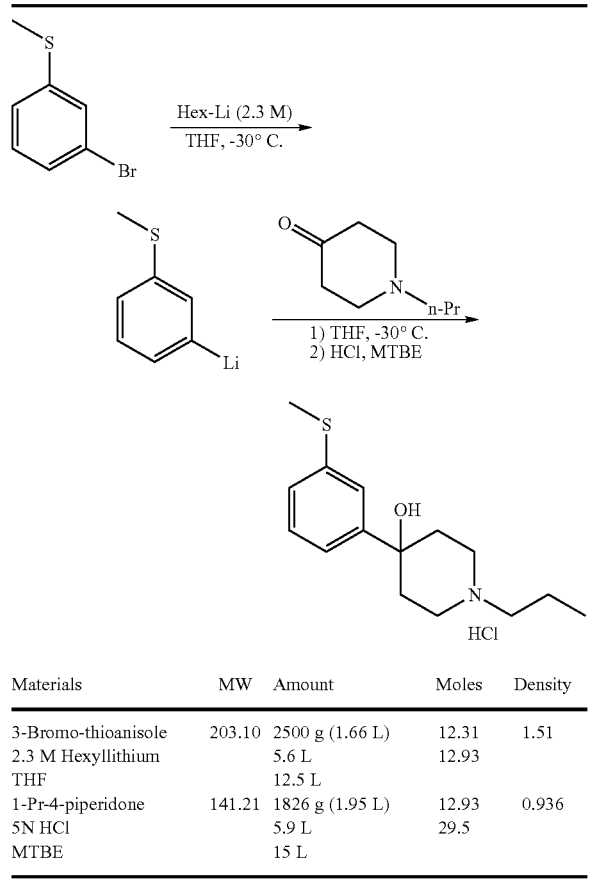

| Materials | MW | Amount | Moles | Density |
|---|---|---|---|---|
| 3-Bromo-thioanisole | 203.10 | 2500 g (1.66 L) | 12.31 | 1.51 |
| 2.3 M Hexyllithium | | 5.6 L | 12.93 | |
| THF | | 12.5 L | | |
| 1-Pr-4-piperidone | 141.21 | 1826 g (1.95 L) | 12.93 | 0.936 |
| 5N HCl | | 5.9 L | 29.5 | |
| MTBE | | 15 L | | |

To a −45° C. solution of 3-Br-thioanisole in THF was added Hex-Li over 1 h with the reaction temperature maintained <−35° C. throughout the addition. Upon completion of the addition, the batch was assayed for conversion of starting material to aryl-lithium. Batch was held at −35 to −45° C. until <0.5 A % of 3-Br-thioanisole. 1-Propyl-4-piperidone was slowly added to the −45° C. batch with the reaction temperature maintained <−35° C. throughout the addition. Upon completion of the addition, the addition funnel was rinsed with THF and the reaction aged for 10 min @<−35° C. The reaction was quenched with 5N HCl with the temperature maintained <20° C. during the quench. MTBE was added to the slurry that formed and the mixture was cooled to 0° C. and aged for 30 min. The slurry was filtered and the solids were washed with MTBE (1×5 mL/g vs. starting Br-thioanisole). The filter-cake salt was dried under $N_2$.

EXAMPLE 2

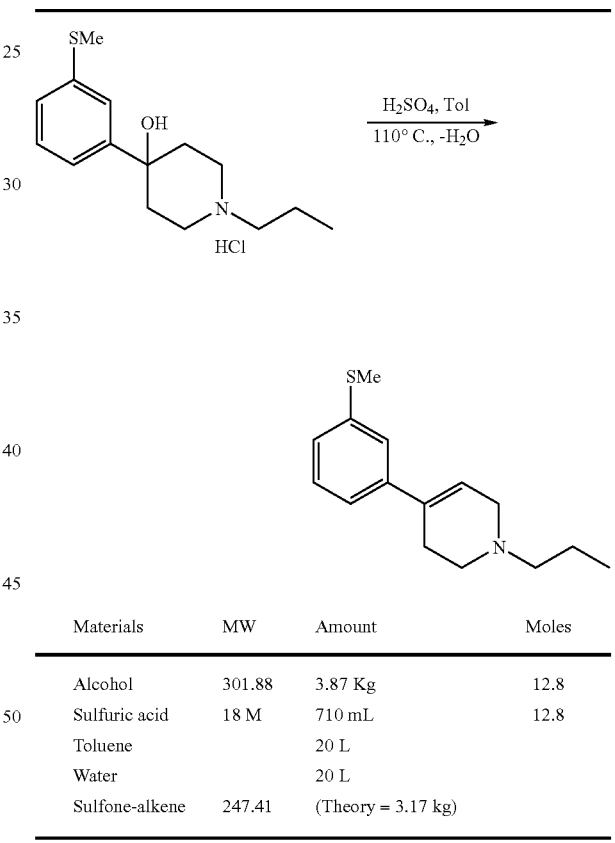

| Materials | MW | Amount | Moles |
|---|---|---|---|
| Alcohol | 301.88 | 3.87 Kg | 12.8 |
| Sulfuric acid | 18 M | 710 mL | 12.8 |
| Toluene | | 20 L | |
| Water | | 20 L | |
| Sulfone-alkene | 247.41 | (Theory = 3.17 kg) | |

The alcohol was slurried in toluene and sulfuric acid was added. The reaction was heated at reflux for 1-2 h with azeotropic removal of water. Upon completion, the reaction was cooled to 70° C. and water was added. The reaction was cooled to RT and the phases are separated. To the aqueous phase was added toluene (6 L/kg) and 5N NaOH (2 eq., ~1.6 L/kg, pH>9) while maintaining temperature <30° C. The phases were separated and the organic phase was treated with 1N sulfuric acid (1 eq. $H_2SO_4$, ~8 L/kg, pH~1). The phases are separated and the aqueous phase was carried directly to the oxidation reaction.

EXAMPLE 3

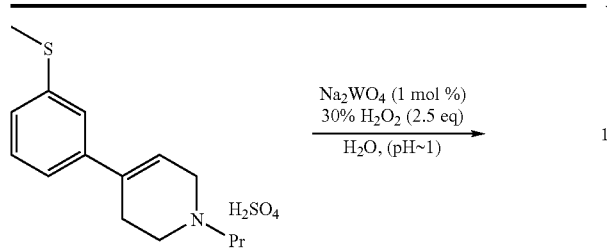
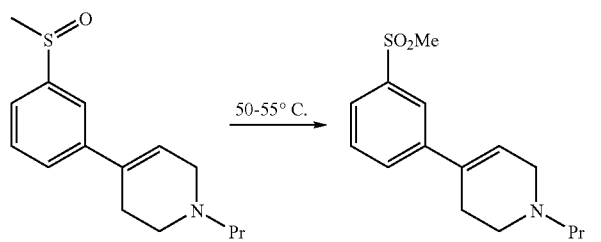

| Materials | MW | Amount | Moles | Density |
|---|---|---|---|---|
| Sulfide-alkene | 247.41 | 3.30 kg | 13.34 | |
| Na$_2$WO$_4$ x 2H$_2$O | 329.85 | 43.9 g | 0.133 | |
| 30% H$_2$O$_2$ | 34.01 | 3.78 kg (3.41 L) | 33.35 | 1.110 |
| 5N NaOH | | 5.6 L | 12.0 | |
| (1.5 ml/g Theory) | | | | |
| 1N NaOH | | 5.6 L | | |
| 20% Brine | | 5.6 L | | |
| toluene (5 ml/g Theory) | | 19 L | | |
| n-heptane | | 22.4 L | | |
| Sulfone-alkene | 279.41 | (Theory = 3.73 kg) | 13.34 | |
| Na$_2$SO$_3$ | 126.04 | 0.84 kg | 6.67 | |

To a solution of sulfide-alkene in aqueous H$_2$SO$_4$ was added Na$_2$WO$_4$×2H$_2$O. H$_2$O$_2$ (30%) was added over 0.5 to 1 h while maintaining temperature below 55° C. The resulting mixture was aged at 50-55° C. until the sulfoxide intermediate was <0.5 A % (1-2 h). The resulting mixture was cooled to 10° C. and toluene (5 L/kg) followed by 5N NaOH was added while maintaining the internal temperature <30° C. The aqueous layer was cut and the toluene layer washed with 1N NaOH, followed by a wash with 20% brine. The toluene layer typically assays at 85-90% yield. The reaction was concentrated to 3 ml/g total volume (10 L) during which time the sulfone-alkene crystallized from solution. The solution was warmed to 50-55° C. and heptane (3 mL/g) was added while maintaining the internal temperature at 50-55° C. To the resulting solution was added more heptane (3 ml/g) at 50-55° C. over 1 h. The resulting slurry was cooled to 23° C. over 0.5 to 1 h, aged 0.5 h and filtered at rt. The filter-cake washed with 1:3 toluene/heptane (4 mL/g, 12 L) and then dried at 50° C. under vacuum with an N$_2$ purge. Typical yield was 75-80%, with >99 wt. % and 99 A % purity. To the combined aqueous layers (aq layer after 5N NaOH, after 1N NaOH wash, after 20% brine wash) at 23° C. was added solid Na$_2$SO$_3$ until peroxide test was negative by Quantofix test strips. An exotherm of ~3° C. occurs.

EXAMPLE 4

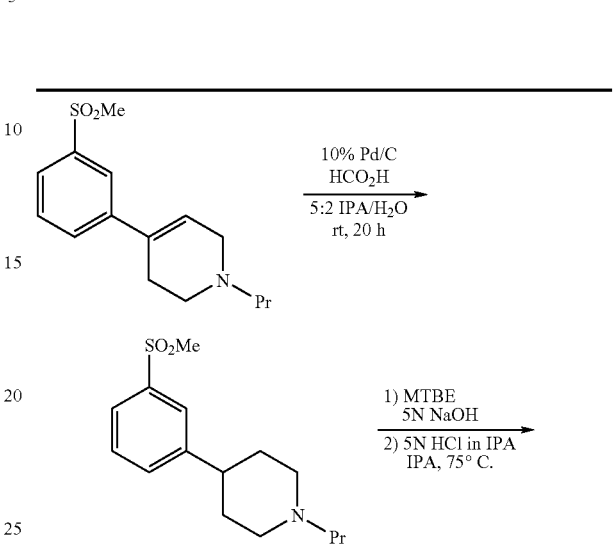
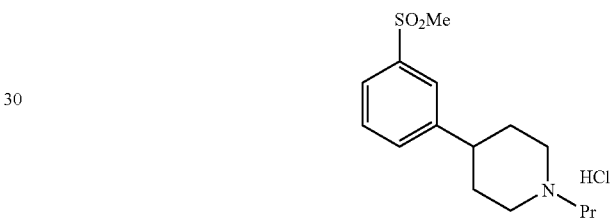

| Materials | MW | Amount | Moles | Density |
|---|---|---|---|---|
| Sulfone-alkene | 279.41 | 3.00 kg | 10.74 | |
| 10% Pd/C | | 600 g | | |
| HCO$_2$H | 46.02 | 2.47 kg (2.03 L) | 53.68 (5 eq.) | 1.22 |
| IPA | | 15 L | | |
| H$_2$O | | 6 L | | |
| Free base | 281.41 | (Theory = 3.02 kg) | 10.74 | |
| 5N NaOH | | 7.5 L | 37.58 (3.5 eq.) | |
| MTBE (10 ml/g) | | 30 L | | |
| H$_2$O (3 ml/g) | | 9.0 L | | |
| 5N HCl in IPA | | 2.58 L | 12.88 (1.2 eq.) | |
| IPA (9.2 mL/g) | | 27.6 L | | |
| HCl salt | 317.88 | (Theory = 3.41 kg) | 10.74 | |

To a slurry of sulfone-alkene in IPA was added HCO$_2$H (5 eq.). To the resulting solution was added a suspension of 10% Pd/C in water (5 ml/g). The suspension was aged at RT for 16 to 24 h until sulfone-alkene was <0.10 A %. The batch was filtered through a pad of solka floc and the filter-cake was rinsed with 1:1 IPA/water (2 mL/g). Typical assay of the combined filtrate and rinse was 95-98% yield. The filtrate was transferred to a 100 L extraction vessel containing 5N NaOH and MTBE pre-cooled to 15° C. The aqueous phase was separated and the MTBE phase washed with H$_2$O (3 mL/g). The MTBE layer was concentrated to 4 ml/g total volume (12 L), flushed with IPA (2×5 ml/g) to remove MTBE and water, then diluted to 9 ml/g in IPA (typical H$_2$O content=0.5 to 1%). The filtrate was warmed to 65° C. and 5N HCl in IPA was added. The resulting slurry was warmed to 75-80° C. until all solids dissolved. The solution was slowly cooled and seeded with pure HCl salt at 65-70° C. The slurry was aged at 65-70° C. for 1 h and then slowly cooled to 23° C. over 1 h. The slurry was filtered, washed with IPA (3 ml/g), and dried over N$_2$.

What is claimed is:

1. A process for preparing a compound of the formula I:

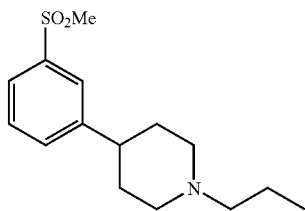

or a pharmaceutically acceptable salt thereof, which comprises:
oxidizing a sulfide of the formula II:

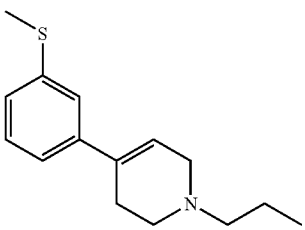

with a catalytic oxidizing agent and an oxidant;
to give a compound of the formula III:

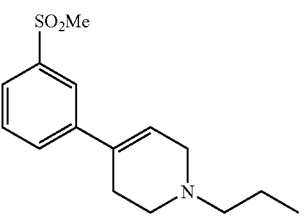

followed by catalytic reduction of the compound of the formula III;
to give the compound of the formula I:

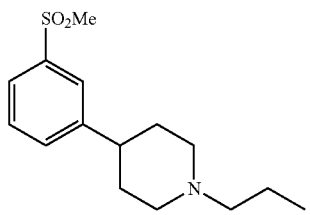

or a pharmaceutically acceptable salt thereof.

2. The process of claim 1 which further comprises:
dehydrating an alcohol of the formula Ia:

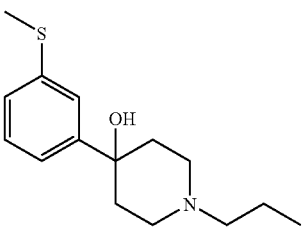

with a strong acid;
to give the sulfide of the formula II.

3. The process of claim 2 wherein the strong acid is selected from sulfuric acid, hydrochloric acid, hydrofluoric acid, nitric acid and trifluoroacetic acid.

4. The process of claim 3 wherein the dehydration of the alcohol of the formula Ia with a strong acid is conducted in solvent selected from toluene, xylene, hexanes and water.

5. The process of claim 1 wherein the catalytic oxidizing agent is a tungsten oxidizing agent.

6. The process of claim 5 wherein the tungsten oxidizing agent is sodium tungstate.

7. The process of claim 1 wherein the oxidant is a peroxide.

8. The process of claim 7 wherein the peroxide is sodium peroxide.

9. The process of claim 1 wherein the step of oxidizing the sulfide of the formula II is conducted at less than 2 pH.

10. The process of claim 1 wherein the step of oxidizing the sulfide of the formula II is conducted at a temperature between 40° C. and 60° C.

11. The process of claim 1 wherein the catalytic reduction of the compound of the formula III comprises catalytic hydrogenation with a palladium catalyst, a platinum catalyst or a ruthenium catalyst.

12. The process of claim 11 wherein the catalytic reduction of the compound of the formula III comprises catalytic hydrogenation with a palladium catalyst.

13. The process of claim 12 wherein the catalytic reduction of the compound of the formula III comprises catalytic hydrogenation with a palladium on carbon catalyst.

14. The process of claim 13 wherein the catalytic reduction of the compound of the formula III comprises catalytic hydrogenation with a 10% palladium on carbon catalyst.

15. The process of claim 14 wherein the step of catalytic reduction of the compound of the formula III is conducted in an aqueous solution with an alcohol.

* * * * *